US00PP20007P2

(12) United States Plant Patent
Jansen

(10) Patent No.: US PP20,007 P2
(45) Date of Patent: May 19, 2009

(54) ***TRICYRTIS* PLANT NAMED 'WHITE WAVES'**

(50) Latin Name: ***Tricyrtis* spp.**
Varietal Denomination: White Waves

(75) Inventor: Robert D Jansen, Beaverton, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/156,828

(22) Filed: Jun. 3, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—Klarquist Sparkman, LLP

(57) ABSTRACT

A new and distinct *Tricyrtis* plant characterized its unique, creamy white centered foliage.

1 Drawing Sheet

Botanical denomination: *Tricyrtis* spp.
Variety designation: 'White Waves'.

BACKGROUND OF THE INVENTION

The present invention relates to a new and distinct *Tricyrtis,* and given the cultivar name is 'White Wave'. *Tricyrtis* is in the family *Liliaceae.* The plant is mutation of *Tricyrtis* 'Imperial Banner' (U.S. Plant Pat. No. 18,956). It was found in tissue-cultured material in Canby, Oreg.

Compared to *Tricyrtis* 'Imperial Banner', the new cultivar has creamy white centers and green margins rather than leaf centers streaked creamy white.

SUMMARY OF THE INVENTION

This new cultivar is characterized by unique, creamy white centered foliage.

This new cultivar has been reproduced only by asexual propagation (division and tissue culture). Each of the progeny exhibits identical characteristics to the new cultivar. Asexual propagation by tissue culture using standard micropropagation techniques with lateral shoots as done in Canby, Oreg. shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a comparison of the foliage of *Tricyrlis* 'Imperial Banner' (on top) and *Tricyrtis* 'White Waves' (on the bottom). Both are 1 year old plants growing in 4 inch containers in the shade house in Canby, Oreg.

DETAILED PLANT DESCRIPTION

The following is a detailed description of the new *Tricyrtis* cultivar based on observations of a two year old specimen grown in a two gallon pot in an open air shade house with 50% shade in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on the Royal Horticultural Society Colour Chart.

Plant:
- *Type.*—Herbaceous perennial.
- *Hardiness.*—USDA Zones 6 to 9.
- *Size.*—Grows to 30 cm wide and 60 cm tall from the top of the soil to the top of the inflorescence.
- *Form.*—With short rhizomes forming a compact clump.

Stem:
- *Type.*—Branched, erect stems.
- *Size.*—Main stem 20 cm to 60 cm long and 2 mm to 4 mm wide, laterals grow to 20 cm long and 2 mm wide.
- *Surface texture.*—Pubescent.
- *Stem number.*—22.
- *Number of leaves per stem.*—3 to 10 main stem leaves with leafy flowering branches from each.
- *Internode length.*—1 cm to 6.5 cm.
- *Color.*—Yellow Green 152B (to Greyed Brown 199B at base on large stems).

Leaf:
- *Type.*—Simple.
- *Shape.*—Elliptic to narrowly elliptic.
- *Arrangement.*—Alternate.
- *Blade length.*—Grows to 10.5 cm.
- *Blade width.*—Grows to 3.5 cm.
- *Margins.*—Entire, pubescent, and strongly undulating.
- *Apex.*—Cuspidate and curling.
- *Based.*—Clasping.
- *Texture.*—Leathery.
- *Surface texture.*—Glabrous on upper surface, bottom surface is pubescent on main veins.
- *Venation.*—Parallel.
- *Color.*—Topside: margins Green 137A, centers Yellow 4D; bottom side: Green 137B except center, Yellow 4D.

Inflorescence:
- *Type.*—Axillary.
- *Number of flowers per stem.*—56 on a 60 cm stem.
- *Number of flowers per cyme.*—1 to 5 for axillary cyme and 1 to 13 for a terminal cyme.

*Pedicel description.*—Grows from 1 cm to 2 cm long, pubescent, Yellow Green 148A.

*Bloom time.*—August to October in Canby, Oreg.

Flower bud:

*Size.*—1.6 cm long and 5 mm wide.

*Shape.*—Oblong, narrowing above the base.

*Surface texture.*—Pubescent.

*Color.*—Greyed Yellow 162D at the bottom ⅓ changing to Greyed Purple 187B on the top ⅓ with the tips Greyed Purple 187A.

Flower:

*Type.*—Actinomorphic, up facing, with segments free.

*Shape.*—Stellate.

*Size.*—Grows to 2.5 cm deep and 3.8 cm wide.

*Texture.*—Waxy.

*Surface texture.*—Glabrous inside, pubescent outside.

*Color.*—White 155A with large 1 mm oval spots of Red Purple 71A.

*Corolla description.*—6 tepals, oblong, entire, reflexed, 2.6 cm long and 5 mm wide, acute, outer tepals with saccate spur at the base.

*Pistil description.*—2.3 cm. long, ovary 2.3 cm long and Yellow Green 145A, style 5 mm long, White 155A with spots of Red Purple 71A, stigma 3-parted, bifid at the tips, glandular, each branch is 7 mm long and colored White 155A with spots of Red Purple 71A.

*Stamen.*—6, filaments 2.4 cm long, White 155A with spots of Red Purple 71A, anthers 2.5 mm long and Greyed Purple 187A, male sterile, no pollen produced.

*Fragrance.*—None.

Fruit:

*Type.*—Capsule.

*Size.*—2 cm long and 3 mm wide.

*Shape.*—Narrowly oblong, 3 angled.

*Color.*—Yellow Green 144D.

Seed: None produced, sterile.

Pest and diseases: Snail and slugs are the main problems on *Tricyrtis*. This new cultivar has leathery waxy leaves and appears to be less appealing to slugs. No other problems have been observed on plant grown under commercial conditions in Canby, Oreg.

COMPARISONS TO SIMILAR *TRICYRTIS*

Compared to the parent plant *Tricyrtis,* 'Imperial Banner', this new variety has leaves that are fully creamy white centered rather than creamy white variably streaked with deep green.

Compared to other variegated *Tricyrtis* on the market, 'White Waves' is unique in having creamy white centered variegation with dark green margins.

I claim:

1. A new and distinct hybrid *Tricyrtis* plant as herein shown and described.

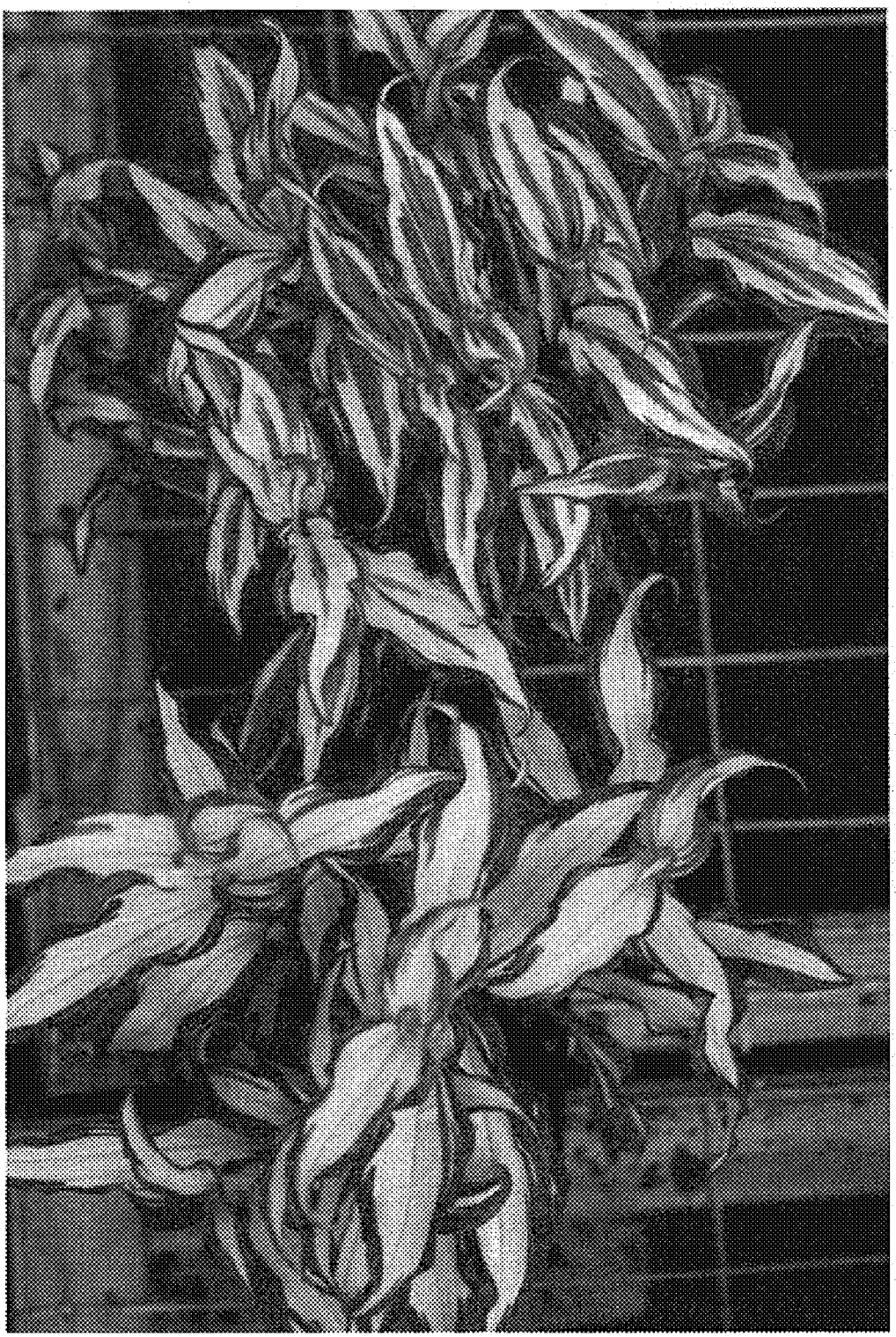

* * * * *